United States Patent [19]

Turner et al.

[11] Patent Number: 5,227,301
[45] Date of Patent: Jul. 13, 1993

[54] IMMORTALIZED BOVINE MANNARY EPITHELIAL CELL LINE

[75] Inventors: Jeffrey D. Turner, Côeau du Lac; Hung Huynh, Ste-Anne de Bellevue, both of Canada

[73] Assignee: The 501 Institution for the Advancement of Learning (McGill University), Montreal, Canada

[21] Appl. No.: 431,294

[22] Filed: Nov. 3, 1989

[51] Int. Cl.$^5$ .................. C12N 5/00; C12N 15/00
[52] U.S. Cl. .................. 435/240.2; 435/172.3; 435/240.1; 435/240.21; 435/948; 935/70; 935/111
[58] Field of Search ............ 435/69.1, 172.3, 240.1, 435/240.2, 240.21, 948; 935/70, 111

[56] References Cited

U.S. PATENT DOCUMENTS 4,808,532  2/1989  Stampfer .................. 435/240.2
5,026,637  6/1991  Soule et al. .................. 435/29

OTHER PUBLICATIONS

Danielson et al., Proc. Natl. Acad. Sci. 81:3756–3760 (1984).
Yasumoto, Mol. Cell Biol. 4(4):712–721 (1984).
Jat et al., J. Virology 59(3):746–750 (1986).
R. S. Einsenstein et al., Molecular and Cellular Biology, 1988, vol. 8, pp. 3183–3190.
D. Medina et al., Experimental Cell Research, 1987, vol. 172, pp. 192–203.
B Van Deurs et al., The Journal of Histochemistry and Cytochemistry, 1987, vol. 35, no. 4, pp. 461–469.

*Primary Examiner*—Jasemine C. Chambers
*Attorney, Agent, or Firm*—Dressler, Goldsmith, Shore, Sutker & Milnamow, Ltd.

[57] ABSTRACT

The present invention relates to a bovine immortalized mammary epithelial cell line which has normal physiological responses in that it produces milk constituents which comprises α- and β-casein and lactose. There is provided, using the cell line of the present invention a method of 'in vitro' studying lactation. There is provided a method of 'in vitro' screening for gene expression of DNA constructs for transgenic cows, since the cell line of the present invention is a bovine one. The cell line can be further used in a method for indefinitely expressing foreign genes. The cell line of the present invention has been deposited at the ATCC under the accession number CRL 10274.

4 Claims, 1 Drawing Sheet

IMMORTALIZED BOVINE MANNARY EPITHELIAL CELL LINE

BACKGROUND OF THE INVENTION

Establishment of cell lines of mammary epithelial origin is critical for studies on the mechanism of action of lactogenic hormones and as a simple, biologically meaningful 'in vitro' test system for recombinant DNA constructs destined for expression within the mammary glands of transgenic animals. Milk synthesis occurs within clusters of differentiated mammary epithelial cells and is under the strict control of lactogenic peptides and steroid hormones. Initiation of milk synthesis is thereby coordinated temporally with parturition. The molecular mechanisms by which hormones stimulate and maintain lactation are poorly understood. Post-transcriptional regulation appears to be of primary regulatory significance (Goyette, W. A. et al., Cell (1979) 17:1013; Eisenstein, R. S. and Rosen, J. M., Mol. Cell. Biol.(1988) 8:3183. In mice, prolactin increases the half-life of casein mRNA by some 17 to 25 fold while gene transcription increases by 2 to 4 fold (Goyette, W. A. et al. (1979) idem). Complimentary work with any agricultural dairy species is completely lacking.

Industrial production of proteins using the powerful biosynthetic capacity of the bovine mammary gland is an emerging technology. Mammary epithelial cells within the bovine udder produce over a kilogram of protein daily. This complex protein contains many post-translational modifications. Transgenic animals in which foreign genes are expressed in the mammary gland, offer a method of producing heterologous proteins without the restrictions of prokaryotic fermentation. The major barrier to exploiting this concept are the inadequacies of germ line manipulation in farm animals. Problems include modest expression of transgenes, and poor tissue specific expression. A gene expression screening system which could identify superior gene constructs prior to gene transfer, would improve transgenic animal production.

It would be highly desirable to have established mammary cell lines which demonstrate hormone responsiveness and enhanced secretory capacity. They would offer an unparalleled system to explore novel constructs within the target organ, the mammary gland of livestock species. Large numbers of recombinant DNA constructs can be rapidly assessed at modest cost.

Established cell lines should be clonal and capable of either continuous proliferation or differentiation depending on the hormonal and extracellular matrix signals. A transformed phenotype showing growth in soft agar or tumorigenicity is not desirable. Despite considerable development, no single cell line derived from mammary epithelial presents these attributes. The murine COMMA-D cell line exhibits mammary-specific differentiation when exposed to the appropriate extracellular matrix (ECM) and lactogenic hormones (Eisenstein, R. S. and Rosen, J. M.(1988) idem). However, this cell line is heterogeneous being composed of at least 3 cell types of which only 10–20% are capable of casein synthesis. Subcloning COMMA parental lines leads to a loss of prolactin responsiveness (Medina, D. et al., Exp. Cell. Res. (1987) 172:192) or a loss of ECM requirements and protein secretion (Ball, R. K. et al., Embo. J. (1988) 7:2089).

Spontaneous bovine mammary epithelial cells (BMEC) in long term culture have been reported to differentiate (Schmid, E. et al., J. Cell. Biol. (1983) 96:37). However, lactose and casein secretion is low and not inducible with prolactin (our unpublished data).

A variety of established human breast carcinoma lines exist T97D, MCF-7 (Van Deurs, B. et al., J. Histochem. (1987) 35:461), but these appear to be transformed and show variable expression of differentiate phenotype such polarity, tight functions and secretion of milk specific constituents.

It would be highly desirable to have an immortalized mammary cell line which would have normal physiological responses and hence would not be transformed.

Such a cell line would provide one skilled in the art with an 'in vitro' system to study lactation, a gene expression system to screen DNA constructs prior to gene transfer and with a method of indefinitely expressing foreign genes.

SUMMARY OF THE INVENTION

Surprisingly and in accordance with the present invention, there is provided a bovine immortalized mammary epithelial cell line having normal physiological responses in that it produces milk constituents which comprises $\alpha$- and $\beta$-casein and lactose.

The cell line of the present invention is immortalized but not transformed and hence behave in a normal physiological way except for its immortal property.

This mammary cell line provides a method of studying 'in vitro' lactation due to its normal physiological responses.

The bovine cell line of the present invention has been deposited at the ATCC under the accession number CRL 10274. Such a bovine cell line provides a method of 'in vitro' screening for gene expression in transgenic cows prior to gene transfer when the mammary gland is the target organ for expression. The testing of DNA constructs prior to gene transfer reduces tremendously the cost of genetic engineering.

The cell line of the present invention also provides a method for indefinitely expressing foreign genes.

IN THE DRAWINGS

FIGS. 1A–1C show an indirect immunofluorescent visualization of $\alpha_S$ and $\beta$-casein with prolactin (A), without prolactin (B) and without casein specific primary antibody (C).

DETAILED DESCRIPTION OF THE INVENTION

Figure 1A:
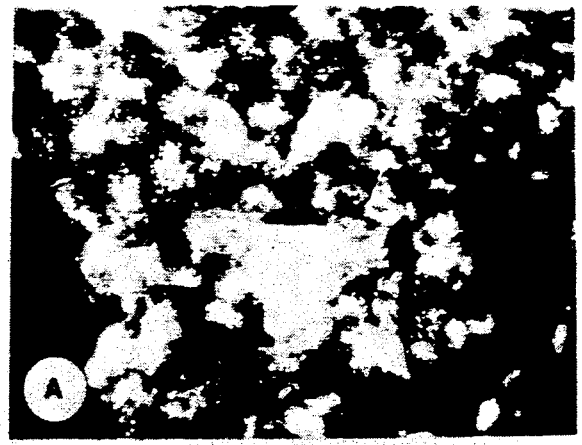

The hallmark of differentiated mammary epithelial cells is copious secretion of milk specific components regulated by lactogenic hormones. We describe an established clonal cell line produced from primary bovine epithelial cells by transfection with SV-40 large-T-antigen designated (MAC-T). Differentiation was induced by augmenting cell-to-cell interactions on a floating extracellular matrix in the presence of prolactin. The differentiated phenotype was characterized to include 1) increased abundance of $\beta$-casein mRNA; 2) increased number and size of indirect immunofluorescent casein secretory vesicles; 3) $\alpha_S$ and $\beta$-casein secretion; and 4) increased lactose secretion. The established cell line of the present invention will facilitate studies on the cell biology of the mammary gland and will provide an 'in vitro' screening system for DNA constructs destined for genome manipulation where the mammary gland is the target organ for expression.

Experimental Procedures

Cells

Primary mammary gland cells were obtained by asceptic biopsy from lactating Holstein cows at slaughter and dissociated as described by Burwen, S. J. and Pitelka, D. (Exp. Cell. Res. (1980) 126:249). Mammary tissue was minced, placed in a trypsinizing flask to which was added 1:10 (w/v) dissociation media (1×Hank's Buffered Saline solution, 11 mM glucose, 4% bovine serum albumin and collagenase 200 IU/ml) and rotated at 200 rpm for 60 min at 37° C. Single primary cells obtained by filtration through 150 um Nitex screens were washed with Dulbecco's phosphate buffered saline (DPBS) and grown in Dulbecco's Modified Eagles Media (DMEM), 20% fetal calf serum (FCS), 5 ug/ml insulin, 1 ug/ml hydrocortisone, 100 IU/ml penicillin and 100 ug/ml streptomycin on tissue culture plastic with 5% $CO_2$ and 100% humidity at 37° C.

Prior to transfection, cells were dilution cloned and colonies arising from single cells with epithelial morphology were selected. These cells were sensitive to Geneticin ® (G418 sulfate) such that 200 ug/ml resulted in 100% mortality.

Bovine mammary epithelial cells of the hormone-adapted BMEC+H clonal cell line were obtained from W. W. Franke (German Cancer Research Center, Heidelberg, F. R. G.). These cells were used as a positive control for immunohistochemical identification of epithelial cells and as a cell line for comparison of synthetic capability. Cells were grown in DMEM supplemented with 20% FCS, insulin, hydrocortisone and prolactin (1 ug/ml) on plastic (Schmid, E. et al. (1983) idem). Synthetic and secretory capacity of BMEC cells was assessed on floating collagen gels in the same way as our experimental mammary cell lines.

The P160 cell line was a v-abl transformed NIH 3T3 cell line obtained from J. C. Bell (University of Ottawa, Canada). They were grown in complete media; removed with trypsin, washed twice in $Ca^{++}$ free phosphate-buffered saline and $5 \times 10^5$ cells/100 $\mu$l injected into nude mice to serve as a positive control for the turmorigenicity assay.

DNA Transfection

Transfections were undertaken with adherent cells ($1.3 \times 10^5/cm^2$) using 10 $\mu$g pBAPSV40TtsA58 and 10 $\mu$g PSV2-neo per $1 \times 10^7$ cells by the calcium phosphate procedure of Graham, F. L. and van der Eb, A. J.(Virol. (1973) 52:456). After 4 h of transfection, the cells were washed once with DPBS and glycerol shocked for 2 min, washed with DPBS and complete media added for 24 h. Cells were then trypsinized and plated in 6 well multiplates ($5.2 \times 10^3$ cells/cm$^2$) in complete media with 400 $\mu$g/ml Geneticin ®. Transfection efficiency averaged 6.5 in $10^5$ cells. Surviving colonies were cloned by dilution and yielded 414 clones of which 250 were expanded and frozen.

Expression of the SV-40 large-T-antigen was directed from the plasmid pBAPSV40TtsA58 obtained from L. Chalifour, Biotechnology Research Institute (Montreal, Canada). This plasmid includes a 4.0 kb human $\beta$-actin promoter and a 0.75 kb SV-40 polyadenylation sequence and a 2.6 kb Bam HI fragment of SV-40 large-T-antigen (Jat, P. S. and Sharp, P. A. Mol. Cell. Biol. (1989) 9:1672). The pSV2-neo plasmid (Southern, P. J. and Berg, P., J. Mol. Appl. Gen. (1982) 1:327) was provided by G. Matlashewski, McGill University, Montreal and confered antibiotic resistance to Geneticin ®.

This bovine immortalized mammary cell line has been deposited at the ATCC under the accession number CRL 10274 and is designated as the MAC-T cell line.

Hormone-responsiveness to Prolactin

Cloned cells with good growth characteristics were evaluated with regard to their hormone responsiveness to prolactin. Parameters evaluated included 1) intracellular casein accumulation by immunohistochemistry; 2) casein secretion by Western blotting; 3) $\beta$-casein mRNA abundance by Northern blotting; and 4) lactose secretion using an enzymatic assay. Cells were plated at high density ($9 \times 10^4$–$1.8 \times 10^5$ cells/cm$^2$) on calf tail collagen gels prepared as per Emerman, J.T. and Pitelka, D., (IN VITRO (1977) 13:316). After 12 to 14 hours, dead cells were removed with two DPBS washes and media (DMEM, 5 ug/ml insulin, 1 ug/ml hydrocortisone and 2.5% FCS) supplemented with 5 $\mu$g/ml prolactin (USDA-6PRL-B-I) added and the gels were then released to float in this media. Aliquots of media were removed at 24, 36 and 48 h and 72 h after prolactin addition, and analyzed for lactose and casein content.

Lactose concentrations in media was measured using commercially available methods (Boehringer-Mannheim GmbH) with the following modifications; corrections were made for the presence of phenol red and 20 $\mu$l of a standard lactose solution (0.503 g/l) was used to spike each sample into the linear range of the standard curve.

Evaluation of $\alpha$ and $\beta$ casein within the media was evaluated by Western immunoblotting techniques and within cells by immunofluorescent cytochemistry. Proteins within the media were separated using SDS-PAGE, through 4% stacking gel and 10% separating cell (Laemmli, U. K., Nature (1970) 277:680). Gels were transferred by electroblotting to nitrocellulose filters (70 V, 3 h, 4° C.) and washed briefly in $H_2O$ then 20 mM Tris pH 7.5, 500 mM NaCl (TBS), blocked with 3% gelatin in TBS for 60 min then washed twice in TBS with 0.05% Tween 20 ® (TTBS). Rabbit anti-bovine antibodies to $\alpha$ and $\beta$ casein were diluted (1:2000) and incubated overnight in TTBS plus 1% gelatin. After two TBS washes, the filter was transferred to the second antibody goat anti-rabbit IgG conjugated to alkaline phosphatase (1:2000) for 60 min. Filters were washed twice with TTBS then TBS to remove Tween-20 ® and developed as recommended by Bio-Rad.

Total cellular RNA was extracted from cells grown on plastic and on collagen using the procedure of Towle, H. C. et al., Biochemistry (1980) 19:579). The integrity of each sample was verified by gel electrophoresis and the quantity determined spectrophotometrically. Northern blots were performed after capillary transfer of glyoxylated total RNA from a 1.5% agarose gel onto Zetaprobe ® membrane (Bio-Rad). Bovine $\beta$-casein cDNA (Pst 1,1150 bp, J. P. Mercier, INRA France) and bovine $\beta$-actin cDNA (Degen, J. L. et al. J. Biol. Chem. (1983) 258:12153) were labelled by oligolabelling, denatured and used as hybridization probes.

Immunohistochemistry

Immunohistochemistry was used to 1) identify MAC-T cell lineage and 2) define prolactin effects on intracellular casein levels. Monoclonal antibodies (MAb) which react with cytokeratin (Jahn, L. et al., Differentiation(1987) 36:234; type II, subfamily No 1-8) and vimentin (Jahn, L. et al. (1987) idem) were used to characterize cell type as epithelial or stromal, respectively. When cells were grown on eight well chamber slides (plastic substrata), fixation and staining could be completed directly using manufacturers recommendations. Cells on collagen were briefly treated with collagenase and then plated on plastic for 30 min prior to staining. Immunofluorescent localization of the primary antibody was accomplished using a second antibody, goat anti-mouse Ig-FITC conjugate. Positive biological control for cytokeratin staining were the BMGE cells which show a characteristic pattern (Schmid, E. et al. (1983) idem). Incubation of cells with FITC-goat anti-mouse IgG alone failed to result in cell staining.

Samples were directly visualized with a Jenalumar microscope, at 400× magnification, equipped with epifluorescence optics and appropriate excitory and barrier filters for FITC.

Antibodies directed toward bovine casein were used to assess whether exogenous prolactin would increase the casein content within MAC-T cells. Caseins ($\alpha_S$, and $\beta$) were purified by DEAE-cellulose chromatography from acid precipitated casein (Davies, D. T. and Law, A. J. M., J. Dairy Sci.(1977) 44:213), then emulsified with an equal volume of complete Freund's adjuvent and one ml (1 mg protein) injected intradermally into male New Zealand White rabbits (Charles River, Inc.). Booster injections of incomplete Freund's adjuvent were given monthly for two months. Serum was discomplemented by incubation at 56° C. for 30 min then aliquots frozen. Antibodies were diluted 1:5 in PBS before use.

Secondary antibody, a goat anti-rabbit Ig-FITC (Boehringer-Mannheim GmbH) was used to locate casein containing vesicles within cells. Differentiated cells on collagen were briefly dissociated with mild collagenase treatment, and allowed to adhere in chambers slides, after which they were fixed and examined for immunologically reactive material.

Establishment Characteristics

Tumorigenic potential, growth on soft agar and the presence of large-T-antigen were used to evaluate the nature of MAC-T cells. Tumorigenicity was evaluated by injecting $5 \times 10^6$ cells/100 $\mu$l DPBS subcutaneously into 28-40 day-old Nu/Nu CD-1 homozygous mice (Charles River Inc.). As a positive control P160 cells were also injected ($5 \times 10^5$ cells/100 $\mu$l) at a different site. Mice were palpated for the presence of tumors after 8 weeks. Growth in soft agar was evaluated by placing 600 cell/ml on 0.3% agarose in complete media. Any colonies present after 16 days were counted.

Monoclonal antibodies to SV-40 large-T-antigen were provided by G. Matlashewski. These MAb was used at a dilution of 1:1 using the aforementioned methods with MAC-T cells attached to plastic and growing.

The MAC-T cells can exist in either a proliferative or in a differentiated phenotype depending on exogenous hormones and extracellular matrix.

Concerning growth characteristics, when MAC-T cells are grown on tissue culture plastic, they show a doubling time of ~17 h and reach confluency at $4.2 \times 10^5$ cells/cm$^2$. These cells show contact inhibition and do not overgrow, but form a uniform pavement of closely associated cells. Conversely, when plated at half confluency on floating collagen gels in the presence of prolactin, cell growth expressed as total DNA concentration remains unchanged over 5 days. Difficulties in quantitatively removing cells from collagen gels was the reason for using DNA content as an indirect measure of cell number.

Phase contrast microscopy illustrated that MAC-T cells have characteristic epithelial morphology, growing in monolayers similar to those formed by primary epithelial cultures. Evidence of epithelial cell lineage was the characteristic array of cytoskeletal proteins, namely intermediate filaments which are clearly defined by indirect immunofluorescence with MAb's recognizing cytokeratin. The fluorescent pattern was very similar to those for the BMGE cells, a spontaneous established cell line of mammary gland origin (Schmid, E. et al. (1983) idem). Omission of the primary antibody abolished the immunofluorescent pattern. The absence of significant vimentin signal located within MAC-T cells indicated that they are not contaminated with fibroblasts or adipocytes. This was not surprising as the MAC-T cells are clonal in origin.

Nature of Establishment

The best evidence of establishment is long-term growth in culture without senescence or crisis. The MAC-T cells are currently >150 passages, which represents continuous culture for more than one year. In contrast, the primary cultures typically enter crisis between 20-50 passages. The extended growth of MAC-T cells appears to reflect establishment rather than oncogenic transformation. MAC-T cells are uniformly non-tumoriogenic 0/7 when injected into immunodiffencent mice. This result appears to be a true negative, as P160 cells initiated prompt tumor growth within control animals. The growth habit of the cells also argues for establishment as opposed to transformation. MAC-T cells do not overgrow or form foci and have an obligatory requirement for fetal calf serum mitogens, at a level of 5% supplementation. These cells are anchorage dependent as they do not grow on soft agar.

Transfection with SV-40 large-T expressing plasmids appears to be responsible for maintaining the established phenotype. Southern analysis confirms the presence of the SV-40 large-T antigen within the genome of the MAC-T cells. Expression of large-T antigen gene assessed by indirect immunofluorescence, indicated a low level constitutive expression. The low levels of SV-40 large-T antigen are sufficient to immortalize the cells but not prevent differentiation when prolactin and extracellular matrix are present. Although the pBAPSV40TtsA58 plasmid has been shown to regulate cell proliferation in a temperature dependent way when integrated into the genomes of other cell types, MAC-T cells did not demonstrate fluctuations in large-T signal or growth rate when grown at 33° or 39.5° C.

MAC-T Cell Characteristics

The MAC-T cell line of the present invention is hormone-responsive. The choice of bovine mammary gland as a starting point is obvious. The dairy industry relies on milk produced from a single epithelial cell type, without having an established cell line as an 'in vitro' model. This discussion will focus on characterization of the MAC-T cell line including the nature of cell establishment and morphology, and growth characteristics and the differentiation potential, and prolactin sensitivity.

Establishment of MAC-T cells appears the result of constitutive low level expression of the SV-40 large-T antigen. This gene was located within the MAC-T genome and MAb's detect large-T antigen protein within the cells. Large-T antigen has previously been extensively used to establish primary rodent fibroblasts (Jat, P. S. and Sharp, P. A. (1989) idem; Rassoulzadegan, M. et al., PNAS (1983) 80:4354). The presence of the large-T antigen appears essential for maintenance of the transformed phenotype.

The MAC-T cells are immortalized and not transformed. MAC-T cells demonstrate topoinhibition, even at confluency. Cells within the monolayer are closely opposed and maintain cytoskeletal contact via desmosomes. MAC-T cells are anchorage dependent as shown by the absence of growth on soft agar. MAC-T cells do not initiate tumors in immuno-deficient mice. These features are consistent with an immortalized cell line.

MAC-T cells exist as two phenotypes which are controlled by exogenous hormones and extracellular matrix. When grown on plastic substrata in the absence of prolactin, the cells divide rapidly and reach confluency at high cell densities. At publication, these cells were >150 passages, which is the best evidence that this is in fact an established line. These growth properties are indispensable for experimentation involving large numbers of cells or transfection where a few positive clones must be grown-up. The second phenotype resembles a differentiated mammary epithelial. When plated on type I collagen in the presence of prolactin, MAC-T cells cease their mitotic activity and began synthesis and secretion of milk specific components.

EXAMPLE I

Study of 'In Vitro' Lactation

Prolactin and Extracellular Matrix Effect MAC-T cells (ATCC accession number CRL 10274)

As lactose and casein proteins are not found in media or serum supplements, their presence in conditioned media is indicative of secretory capacity of differentiated mammary epithelial cells.

Beta-casein mRNA abundance within MAC-T cells responds to both exogenous prolactin and culture on floating collagen gels. MAC-T cells grown on plastic without prolactin show very low levels of β-casein mRNA. Prolonged exposures are required to obtain autoradiographic signals. Attachment to floating collagen gels increases β-casein mRNA abundance by 24 h, initiating a higher steady state level. Exogenous prolactin and collagen leads to an augmented β-casein mRNA abundance, by 48 h. Constant β-actin signal confirms equal loading of total RNA.

Secretion of α and β-casein protein followed a temporal pattern consistent with that observed at the mRNA level. Western blot analysis shows that prolactin causes a strong stimulation of α and β-casein secretion by MAC-T cells on collagen by 48 h. Reflective densitometry gives an approximate 3-fold increase in β-casein secretion at this time. The concentration of β-casein was approximately 250–500 ug/1 × 10$^7$ cells/24 h of conditioned media. In the absence of prolactin, casein secretion was lower and constant. Casein secretion is below the limits of detection when MAC-T cells are grown on plastic without prolactin supplementation.

Figure 1B:
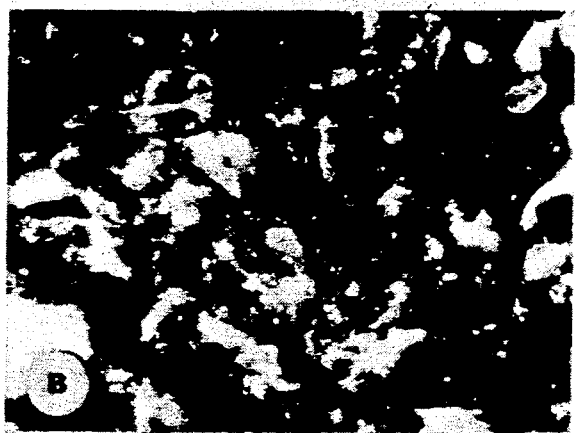
Figure 1C:
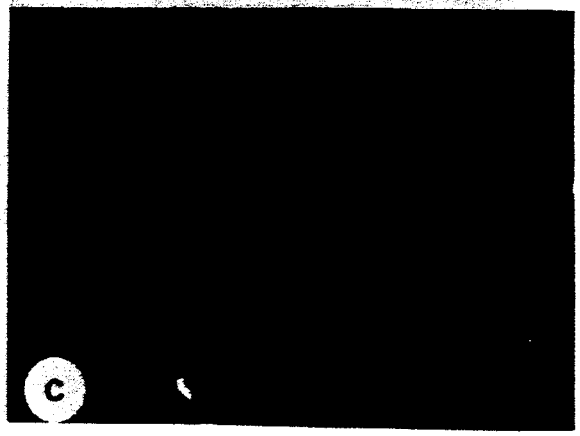

Immunological localization of α and β-casein produced a graphic demonstration of prolactin effects on intracellular casein content (FIG. 1). MAC-T cells exposed to prolactin A) for 48 h were congested with numerous immuno-reactive secretory vesicles. In properly oriented cells, the polarity of these granules with respect to the nucleus is evident. When MAC-T cells were grown on collagen without prolactin, the number of granules was reduced but not completely so (B). The absence of immunofluorescent staining of cells in the absence of primary antibody (C) indicated that these granules were casein-like. Prolactin in conjunction with a floating collagen gel led to the secretion of lactose and caseins. Lactose secretion as measured by lactose accumulation in the media ranged between 2 to 8 nmol/μg DNA/24 h. After 48 h on collagen, lactose secretion leveled off irrespective of prolactin stimulation. Prolactin did not appear to increase the maximum rate at which the MAC-T cells could secrete lactose but did allow for more accumulation within the media.

Secretory Functions

Two major constituents of milk are casein proteins and the dissaccharide, lactose. As neither are found in culture media or serum supplements, their presence in conditioned media is indicative of secretory capacity of differentiated mamary epithelial cells. Casein gene expression and secretion of casein protein are regulated in MAC-T cells by a combination of extracellular matrix and hormonal signals. Concerning extracellular matrix, culturing MAC-T cells on plastic substrata prevented differentiation as defined biochemically. Beta-casein mRNA abundance was very low and α and β-casein secretion was not detectable. Whereas, culture on floating collagen gels produced dramatic increases in β-casein gene expression which began within 24 h and persisted for at least 3 days. Increases in casein secretion followed the rise in mRNA abundance. Sensitivity to substrata is consistent with other mammary epithelial cell lines and primary cells. COMMA-D cells increase casein mRNA abundance on floating collagen gels (Medina, D. et al. (1987) idem; Eisenstein, R. S. and Rosen, J. M. (1988) idem). Similarly primary mouse mammary cells (Emerman et al. 1977) and COMMA-D cells (Danielson, K. G. et al., PNAS (1989) 81:3756) showed an obligatory requirement for a deformable collagenous matrix for the induction and maintenance of casein production. The mechanism by which extracellular matrix controls gene expression has not been investigated with MAC-T cells.

Hormone-responsiveness to prolactin is another characteristic of MAC-T cells. Exogenous prolactin augmented extracellular matrix signals by further increasing casein gene expression. This induction has a lag of at least 24 h with respect to β-casein mRNA abundance and 36 h for casein secretion. Prolactin effects observed in COMMA-D cells (Eisenstein, R. S. and Rosen, J. M. (1988) idem) show a similar pre-induction lag phase following addition of lactogenic hormones.

Lactose secretory function of the MAC-T cell line is comparable to freshly dissociated primary epithelial cells (Burwen, S. J. and Pitelka, D. (1980) idem). When plated on floating collagen gels in the presence of prolactin, lactose secretion in MAC-T cells range between 2–8 nmol/μg DNA/24 h compared to 4–12 nmol/μg DNA/24 h for primary cells. Omission of prolactin attenuates lactose secretion and led to a smaller accumulation of lactose in culture media. A suppression of lactose secretion as indicated by a plateau in media lactose concentration was noted after 48 h of prolactin stimulation and in the absence of prolactin. Similar findings by Burwen, S. J. and Pitelka, D. ((1980) idem) were interpreted as negative feedback regulation on lactose synthesis and secretion. Although the similarities in lactose secretory function between MAC-T and freshly dissociated mammary cells is encouraging, the absolute amount of lactose secreted is small relative to rates observed 'in vivo'. A closer approximation of the 'in vivo' hormonal milieu and a more complete extracellular matrix should improve this 'in vitro' performance.

EXAMPLE II

'In vitro' Screening for Optimizing Eukaryotic Expression Vectors

The current understanding of eukaryotic regulatory elements which regulate tissue specificity and activity of gene expression is inadequate. As such, large upstream fragments of DNA are typically used, in the hope of securing the necessary regulatory sequences (Gordon, K. et al., Bio/Technology, (1987), 5:1183). Our poor capacity to predict promoter or enhancer activity places a premium on a screening system to evaluate the level of expression and tissue specificity of expression. Transgenic mice represent the currently available screening method. These have not been entirely satisfactory due to obvious species differences. For example, a whey acid protein (WAP) is found in rodent milk but not ovine or bovine milk. Therefore, will the WAP promoter be effective for enhancing expression of bovine transgenes even if it is well expressed in mice? Similarly, will the WAP promoter confer tissue specificity for all species?

Established cell lines offer several advantages over transgenic rodent with regard to eukaryotic expression vector screening. They will permit the identification of potentially superior recombinant DNA constructs which can be used with confidence in the production of transgenic animals.

A typical example was recently presented by Doppler, W. et al., (PNAS (1989), 86:104). They examined the hormone responsive elements of the rat β-casein gene which conferred sensitivity to prolactin and glucocorticoids. In this case, a mouse cell line, COMMA-ID subclone HC11, was used to examine a 2300 base pair (bp) 5' flanking region for biological activity. Pools of HC11 were transfected with various 5' deletions ranging from −2300 to +486 (with respect to transcription start site) and the induction of a reporter gene evaluated. The region of −285 to −170 bp was shown to contain strongly inducible promoter elements.

The example includes the following salient points:

1. Introduction of recombinant DNA constructs (vectors) into cells is easy and fast. This example used a calcium phosphate precipitation for DNA transfection, as we have with the MAC-T cells. The pSV2-neo/G418 selection protocol allows for rapid selection.

2. Clonal cell lines provide uniformity of biological systems between plates and between days of experiment. In this example, induction rates could be compared between all of the treatment groups because a clonal cell line was used. Variation is thereby kept to a minimum.

3. Large numbers of constructs could be tested in an economical way. Here, numerous 5' deletion mutants were tested 'in vitro' to locate regulatory elements. The requirement for large numbers of tests was filled with this 'in vitro' system.

EXAMPLE III

Indefinite Foreign Gene Expression

Eukaryotic fermentation is a viable means of overcoming the considerable problems associated with prokaryotic expression of mammalian proteins. Typically, eukaryotic proteins require post-translational modification and the proper folding environment before they are active. An example of such production system was the synthesis of human tissue-type plasminogen activator (PA) within mouse cells reported by Integrated Genetics, now Genzyme (Reddy V. B. et al., (1987) DNA, 6:461). Plasminogen activators are useful as therapeutic agents in thrombolysis. Reddy et al. (1987) created a recombinant DNA construct consisting of the human t-PA gene engineered into a mammalian expression vector. When this construct was transfected into mouse C127 cells, they produced large quantities of authentic human t-PA. This t-PA was immunologically and enzymatically similar to native human t-PA.

The benefits of such an approach are clear.

1. Appropriate recombinant DNA constructs can be transcribed/translated immediately in cell culture to produce authentic proteins. This gives flexibility to produce a large number of products or improve existing production systems.

2. Proteins of interest are secreted into the media where they can be removed. This permits large scale production via eukaryotic fermentation systems with continuous flow.

I claim:

1. An immortalized bovine mammary epithelial cell line prepared by the transfection of primary bovine mammary epithelial cells with the SV40 large T antigen, said cell line having normal physiological responses such that, under hormonal stimulation, produces milk constituents comprising α-and β-casein and lactose.

2. A method of stimulating the production of certain milk proteins by bovine mammary epithelial cells in vitro which comprises the steps of:
 (a) incubating the immortalized bovine mammary epithelial cell line of claim 1 in a culture medium,
 (b) adding to the culture medium one or more lactation hormones to stimulate production of certain milk proteins by said cell line, and
 (c) measuring the amount of α- and β-casein and lactose produced and secreted into the culture medium by said cell line.

3. A method of in vitro screening for foreign gene expression in bovines which comprises the steps of:
 a) providing the immortalized cell line of claim 1;
 b) transfecting the cells of step a) with a foreign DNA construct comprising a bovine casein promoter and a foreign gene wherein the mammary gland is the target organ for said foreign gene expression; and
 c) assaying the transfected cells of step b) for said foreign gene expression; thereby determining the suitability of the foreign DNA construct prior to making a transgenic bovine.

4. The cell line according to claim 1 having the ATCC number, CRL 10274.

* * * * *